(12) United States Patent
Micheva et al.

(10) Patent No.: US 9,008,378 B2
(45) Date of Patent: Apr. 14, 2015

(54) ARRANGEMENT AND IMAGING OF BIOLOGICAL SAMPLES

(75) Inventors: Kristina D. Micheva, San Jose, CA (US); Stephen J. Smith, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1460 days.

(21) Appl. No.: 11/957,143

(22) Filed: Dec. 14, 2007

(65) Prior Publication Data

US 2008/0152207 A1    Jun. 26, 2008

Related U.S. Application Data

(60) Provisional application No. 60/876,046, filed on Dec. 20, 2006.

(51) Int. Cl.
*G06K 9/00* (2006.01)
*G02B 21/36* (2006.01)

(52) U.S. Cl.
CPC .......... *G06K 9/00134* (2013.01); *G02B 21/367* (2013.01)

(58) Field of Classification Search
USPC ....... 382/128; 250/311, 306; 378/4; 600/425; 708/308, 401, 424, 814
See application file for complete search history.

(56) References Cited

U.S. PATENT DOCUMENTS

| | | | | |
|---|---|---|---|---|
| 4,960,330 | A * | 10/1990 | Kerschmann | 356/36 |
| 5,703,056 | A * | 12/1997 | Blasberg et al. | 514/44 R |
| 5,939,278 | A * | 8/1999 | Boon et al. | 435/7.23 |
| 6,531,318 | B1 * | 3/2003 | Palmer-Toy et al. | 436/63 |
| 6,570,952 | B2 * | 5/2003 | Paladini | 378/4 |
| 6,738,529 | B1 * | 5/2004 | Crevier et al. | 382/282 |
| 7,305,110 | B2 * | 12/2007 | Rubbert et al. | 382/128 |
| 7,831,075 | B2 * | 11/2010 | Wilson et al. | 382/128 |
| 2002/0177149 | A1 * | 11/2002 | Rimm et al. | 435/6 |
| 2004/0026630 | A1 * | 2/2004 | Mohun et al. | 250/458.1 |
| 2004/0029213 | A1 * | 2/2004 | Callahan et al. | 435/40.5 |
| 2004/0076319 | A1 * | 4/2004 | Fauver et al. | 382/133 |

(Continued)

OTHER PUBLICATIONS

Rieder, Methods in Cell Biology, 1999, Academic Press, vol. 61, pp. 297-298 and 308-309.*

(Continued)

*Primary Examiner* — Robert Kim
*Assistant Examiner* — Jason McCormack
(74) *Attorney, Agent, or Firm* — Crawford Maunu PLLC

(57) ABSTRACT

High-resolution three-dimensional imaging of a specimen is facilitated. According to an example embodiment of the present invention, a series of very thin slices from a specimen are serially and robustly arranged on an imaging device such as a microscope slide. The slices are imaged and the images are used to reconstruct a three-dimensional image having high resolution at depths into the specimen. The serial arrangement of the slices facilitates the proper ordering of images for reconstruction. Further, the robust nature of the slice arrangement facilitates treatment of the slices and, in some applications, multiple treatments with corresponding imaging sequences for each treatment. Various embodiments are directed to methods and arrangements for three-dimensional characterization of biological specimen and to data that is accessible and/or executable by a computer for linking different images together in order to characterize such biological specimen in three dimensions.

3 Claims, 7 Drawing Sheets

(56) References Cited

U.S. PATENT DOCUMENTS

| | | | |
|---|---|---|---|
| 2004/0135083 A1* | 7/2004 | Kakibayashi et al. | 250/307 |
| 2004/0138549 A1* | 7/2004 | Wintermark et al. | 600/407 |
| 2004/0144923 A1* | 7/2004 | Tanji | 250/311 |
| 2004/0144926 A1* | 7/2004 | Arques et al. | 250/370.01 |
| 2005/0035305 A1* | 2/2005 | Kleinfeld et al. | 250/458.1 |
| 2005/0069541 A1* | 3/2005 | Karlik et al. | 424/143.1 |
| 2005/0085721 A1* | 4/2005 | Fauver et al. | 600/425 |
| 2005/0173632 A1* | 8/2005 | Behar et al. | 250/311 |
| 2006/0019409 A1* | 1/2006 | Nelson et al. | 436/524 |
| 2006/0051736 A1* | 3/2006 | Shields et al. | 435/4 |
| 2006/0183235 A1* | 8/2006 | Hashimoto et al. | 436/86 |
| 2007/0280517 A1* | 12/2007 | De La Torre-Bueno et al. | 382/128 |
| 2008/0081330 A1* | 4/2008 | Kahvejian | 435/6 |

OTHER PUBLICATIONS

Tramu, G. et al. "An Efficient Method of Antibody Elution for the Successive or Simultaneous Localization of Two Antigens by Immunocytochemistry." *The Journal of Histochemistry and Cytochemistry* 1978. 26:4, pp. 322-324.

Blumer, Michael J.F. et al. "Ribbons on Semithin Sections: An Advanced Method with a new type of diamond knife." *Journal of Neroscience Methods* 2002. V. 120, pp. 11-16.

Ren, Ying et al. "Same Serial Section Correlative Light and Energy-filtered Transmission Electron Microscopy." *The Journal of Histochemistry and Cytochemistry* 2003. 51:5, pp. 605-612.

Wali, Naheed et al. "A Method for Collecting Semithin Epoxy Serial Section for Light Microscopy and 3-D Reconstruction." *Journal of Neroscience Methods* 1998. V. 23, pp. 91-94.

Merzel, J. "Preparation of Semithin Serial Sections of Epon Embedded Material." *Experieutia* 1971. V. 27, pp. 611-612.

Basgen, John M. et al. "Comparison of Methods for Counting Cells in the Mouse Glomerulus." *Experimental Nephrology* 2006. V. 103, pp. e-139-e148.

Warshawsky, H. et al. "A Three-dimensional Reconstruction of the Rods in Rat Maxillary Incisor Enamel." *The Anatomical Record* 1971. 169:3, pp. 585-591.

Coulter, H. David et al. "Video-Enhanced Technique for Detecting Neurophysin, Enkephalin, and Somatostatin Immunoreactivity in Ultrathin Sections of Cat Median Eminence." *The Journal of Histochemistry and Cytochemistry* 1986. 34:11, pp. 1405-1415.

Redecker, P. et al. "Syanptophysin—A Common Constituent of Presumptive Secretory Microvesicles in the Mammalian Pinealocyte: A Study of Rat and Gerbil Pineal Glands." *Journal of Neroscience Research* 1993. V. 34, pp. 79-96.

Redecker, Peter et al. "Munc-18-1 and Cystein string protein (CSP) in pinealocytes of the gerbil pineal gland." *Cell Tissue Res* 1998. V. 293, pp. 245-252.

Nanci, A. et al. "Routine Use of Backscattered Electron Imaging to Visualize Cytochemical and Autoradiographic Reactions in Semithin Plastic Sections." *The Journal of Histochemistry and Cytochemistry* 1990. 38:3, pp. 403-414.

\* cited by examiner

US 9,008,378 B2

ARRANGEMENT AND IMAGING OF BIOLOGICAL SAMPLES

RELATED PATENT DOCUMENTS

This patent document claims the benefit, under 35 U.S.C. §119(e), of U.S. Provisional Patent Application No. 60/876,046 filed on Dec. 20, 2006 and entitled: "Arrangement and Imaging of Biological Samples," which is fully incorporated herein by reference.

FEDERALLY-SPONSORED RESEARCH OR DEVELOPMENT

This invention was made with Government support under contract NS054252 awarded by the National Institutes of Health. The Government has certain rights in this invention.

FIELD OF THE INVENTION

The present invention relates generally to the analysis of samples and, more particularly, to the analysis of arranged slices of biological samples.

BACKGROUND OF THE INVENTION

Imaging has played an important part in the analysis of specimen, and in particular, in the analysis of biological specimen. The tools most commonly used for imaging biological molecular architectures are immunofluorescence microscopy (IFM), immunoelectron microscopy (IEM) and genetically encoded fluorescent protein markers and reporters (XFPs). These powerful and widely used tools have led to discoveries that point to the dependence of cell and tissue function upon the very finest details of molecular architecture, and further that demonstrate the extremely variable and dynamic molecular architectures of specimen.

IFM, IEM and XFP imaging methods present challenges, however, and many important aspects of cell and tissue molecular architecture are difficult to explore using previous approaches. For instance, while XFPs have provided unique opportunities for imaging live cell dynamics, they require the expression of transgenes and are thus impractical for the study of human clinical specimens. XFPs also entail substantial probability of perturbing the molecular architectures of interest, and offer generally limited molecular multiplexing capabilities.

While both IFM and IEM are generally confined to use on fixed cells and tissues, these techniques do not require transgene expression, and are thus readily applied to human cell and tissues. IFM provides an ease of use and substantial multiplexing capacity that have made it one of the most widely used tools of cell biology research. However, IFM has generally been limited in resolution and quantitative interpretability.

IEM provides a relatively high resolution and has been useful in its power to discern very fine details of molecular architecture. However, IEM has proven difficult to apply to three-dimensional architectures, has limited multiplexing capacity, and has had very limited volumetric imaging capabilities, particularly as applied to tissue-scale problems.

Generally, imaging specimen, and particular, imaging biological specimen has been challenging.

SUMMARY OF THE INVENTION

The present invention is directed to approaches for imaging a specimen, such as a biological specimen, to facilitate robust lateral and axial resolution. The present invention is exemplified in a number of implementations and applications, some of which are summarized below.

According to an example embodiment of the present invention, an approach to imaging involves the serial arrangement and subsequent imaging of a multitude of thin slices of a specimen. Relatively high-resolution images of the slices are obtained, and the images are combined to create a three-dimensional image for high-resolution views into depths of the specimen.

According to other example embodiments, the present invention is directed to a system for imaging a biological sample. In one such embodiment, a system includes a fluorescence microscope arrangement to image a tissue specimen that is sliced and arranged in an array (e.g., on a glass microscope slide, a glass coverslip or other solid substrate). Data corresponding to the ordering of the tissue slices is stored in a three-dimensional database 540 that indicates (and correlates) data for the individual slices. This data includes, for example, data characterizing the tissue to which the slice applies, the arrangement of slices relative to each slice's location in the array, and any linking data relative to other slides, e.g., where slices of the tissue specimen are arranged on two or more slides (where multiple image-capture tools are used concurrently for reducing image-processing time).

According to other example embodiments, the present invention is directed to computer-accessible (e.g., readable) and/or computer-executable data in a storage medium (such as flash memory and hard drives) from which the data can be retrieved and used to characterize and link sample slices and to facilitate the characterization of a sample from which the slices are obtained. In one application, this characterization is used to arrange and reconstruct images of the slices to display and/or visualize a sample where the images are arranged and used collectively for three-dimensional characterization of specimen.

The above summary of the present invention is not intended to describe each embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1A:
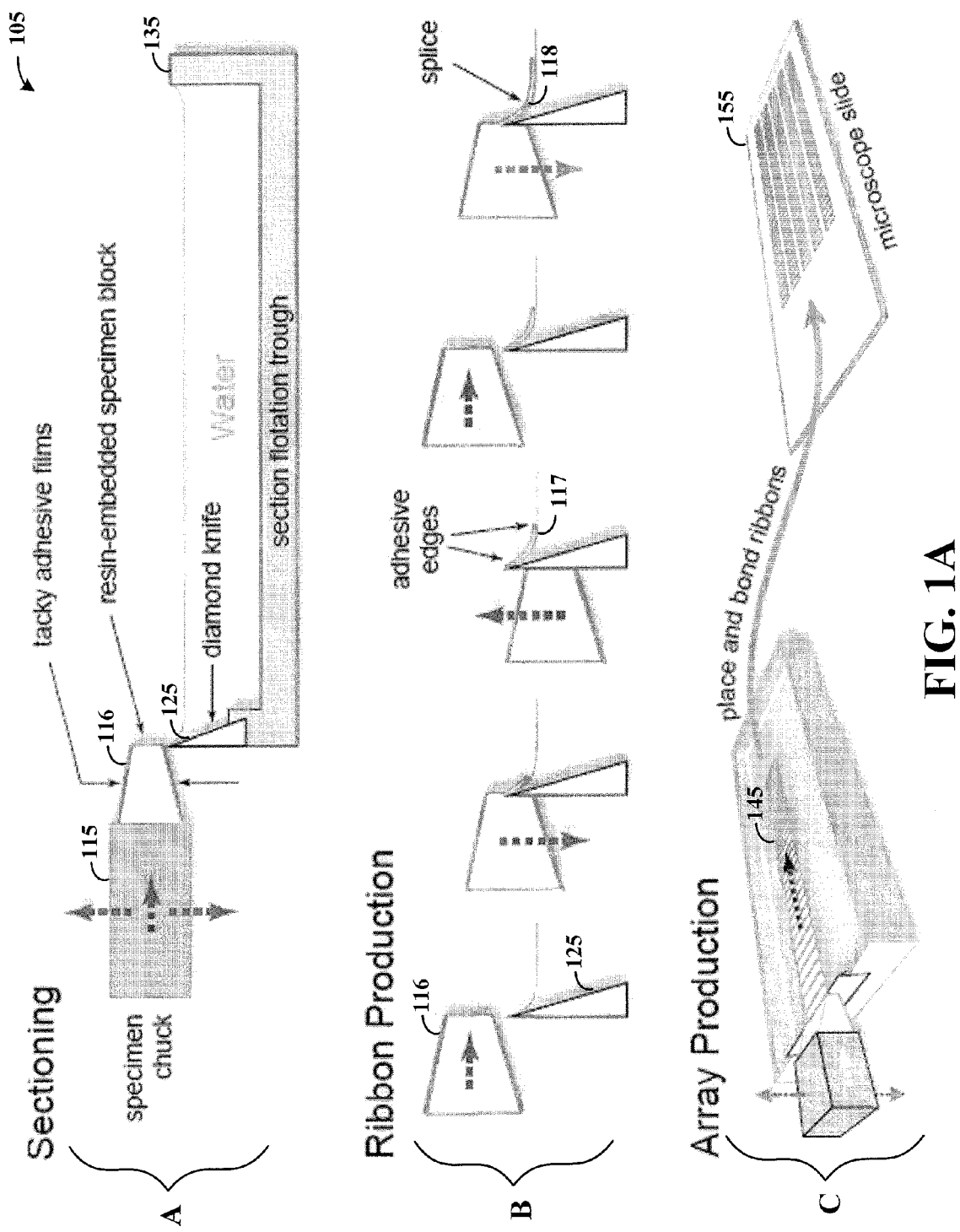
FIG. 1A shows an array tomography arrangement, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of processes, devices and arrangements for imaging, and in particular, to approaches to serially imaging slices of a biological specimen for three-dimensional views of the specimen. While the present invention is not necessarily so limited, various aspects of the invention may be appreciated through a discussion of examples using this context.

According to an example embodiment of the present invention, the molecular architecture of cells and tissues are analyzed by physically sectioning a sample (e.g., a specimen) to make very thin sections of the sample. The thickness of the sections varies with different embodiments; in some applications, the section thickness is in a range of tens to hundreds of microns, and in other applications, the section thickness is similar to the thickness of sections used for electron microscopy (e.g., in a range of about 50-70 nm). A large number of the thin sections are serially arranged on and coupled to (e.g., bonded tightly) an imaging structure such as a glass slide or coverslip. The arranged (e.g., arrayed) thin sections are imaged and the images, together with the known serial arrangement of the sections, are used to create a three-dimensional image of the sample (a.k.a., a tomography image).

A variety of samples are imaged in connection with different embodiments, and the preparation of the samples involving the slicing, arrangement and other preparations also vary accordingly. In one embodiment, fresh tissue is prepared for tomography views by high-pressure freezing and/or chemical fixation and embedding in a hydrophilic acrylic resin, such as LR White resin, commercially available from the London Resin Company of London, England or "Lowicryl" resin, commercially available from Polysciences, Incorporated of Warrington, Pa. The embedded tissue is sectioned using a diamond-knife ultramicrotome, which holds the tissue and controllably advances the tissue against a knife in small (e.g., 30-200 nm) increments to produce continuous ribbons of thin serial sections. The ribbons are bonded in parallel array to the surface of a glass slide, coverslip, or other solid surface.

The resulting two-dimensional array, which may comprise tens, hundreds or thousands of sections, is then stained using labeled antibodies and/or other reagents, taking advantage of the excellent accessibility of epitopes in very thin sections of acrylic to aqueous post-embedding stains. The array of stained sections is then imaged using one or more approaches such as optical fluorescence and/or scanning electron microscopy. Individual two-dimensional section images are aligned and collated into image stacks.

To obtain high quality optical fluorescence images of array sections, it is desirable to use an objective lens of very high numerical aperture and to set up imaging conditions that minimize optical aberrations, for instance by using an oil-immersion planapochromatic objective. It is also desirable, however, to avoid contaminating contact between an array section and immersion oil. In connection with various embodiments, an array fabricated on a glass microscope slide is covered with a separate glass coverslip to avoid such contamination. In some implementations, a mounting medium such as glycerol is placed between the separate coverslip and the array sections to reduce or minimize optical aberrations due to any physical separation between coverslip and array section. In other implementations, an array is fabricated by bonding sections directly to a transparent glass coverslip, and the array is imaged using an oil immersion objective coupled through the coverslip from the surface opposite the array sections.

In some embodiments, the stain is stripped from the two-dimensional array of stained sections after initial imaging, and the sections are re-stained and again imaged. In certain applications, very large numbers of immunostains are multiplexed through repeated cycles of staining, imaging and stripping individual array slides. For instance, in one particular example embodiment, a three-dimensional distribution of antigens in the tissue is reconstructed using an appropriate immunostain applied to the sections. Applied antibodies are subsequently eluted and the sections are re-stained a number of times to facilitate the detection of tens of antigens in the same sample.

Other embodiments involve the combination of an imaging approach as described herein with additional processing to obtain other information about a particular sample. For instance, relative to the above immunostaining approach, one embodiment is directed to the processing of tissue in a way suitable for electron microscopic imaging and, upon completion of the immunofluorescent analysis, the samples are imaged with a scanning electron microscope to obtain high resolution structural information.

In another embodiment, XFP-labeled specimens are imaged in vivo using XFP fluorescence, the specimens are embedded in acrylic resins, and remaining fluorescence in the embedded specimens (subsequently sliced) is used to facilitate imaging via array tomography. This approach facilitates closely correlated immunofluorescence analysis with an array tomography approach for retrospective analysis.

Turning now to the figures, FIG. 1A shows an array tomography arrangement 105 in sectioning, ribbon production and array production views (respectively A, B and C), according to an example embodiment of the present invention. The arrangement 105 includes a specimen chuck 115 that holds a tacky-coated specimen 116, a knife 125 for slicing the specimen and a flotation trough 135 for floating sliced and bonded specimen ribbons. For ribbon production, the knife 125 is moved relative to the specimen 116 to produce a slice 117 of the specimen with adhesive edges (the tacky coating). The adhesive edges stick together to form a splice 118 between each slice of the specimen 116. With this approach, an entire ribbon 145 is produced in the flotation trough 135. Several such ribbons are produced and placed upon a slide 155 to form an array of ribbons for analysis (e.g., for array tomography).

Figure 1B:
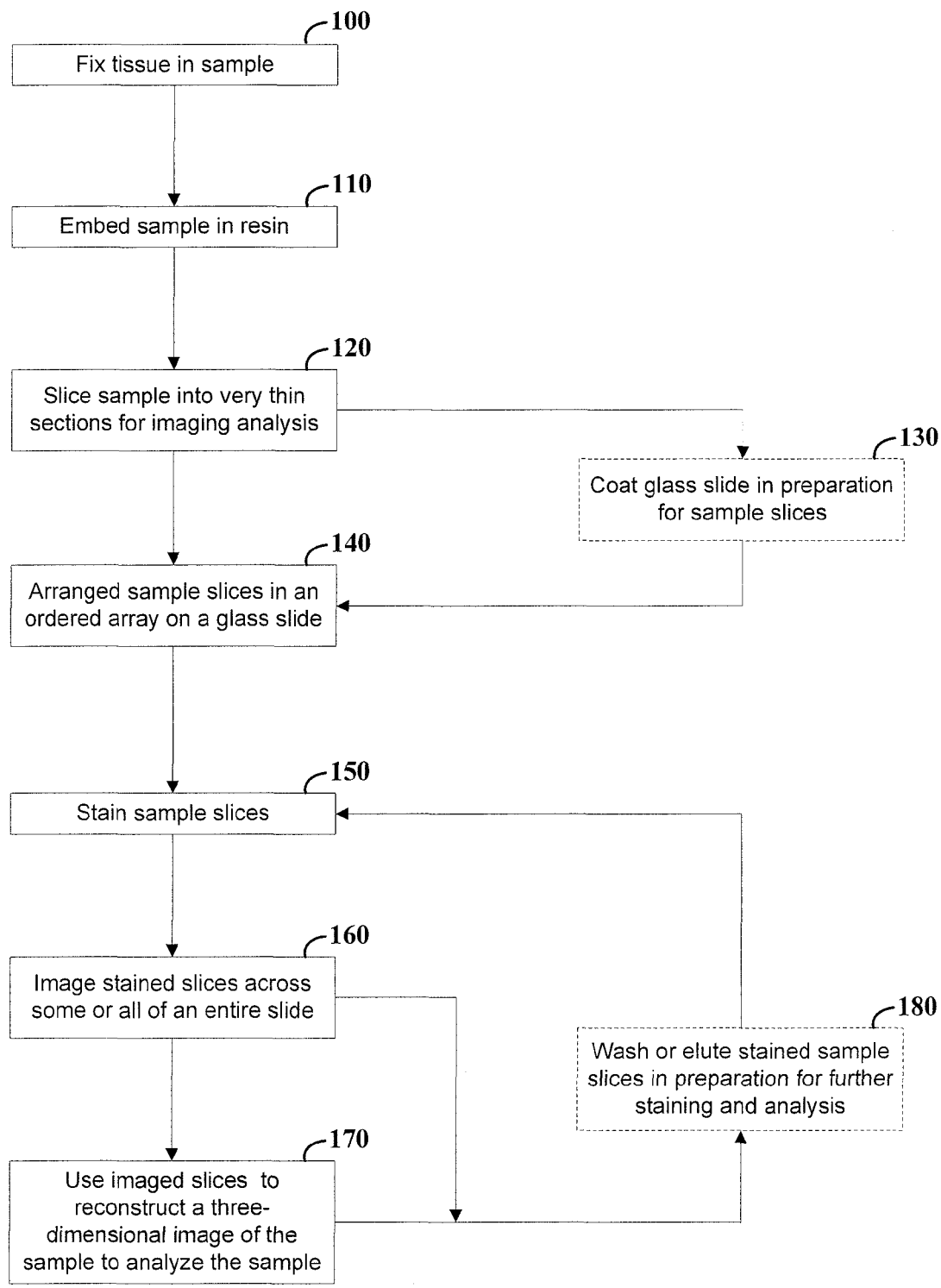
FIG. 1B is a flow diagram for a method of imaging a biological sample, according to another example embodiment of the present invention.

FIG. 1B is a flow diagram for a method of imaging a biological sample such as a biological cell, tissue or organism, such as for assays or proteins, lipids, carbohydrates, messenger RNAs and small molecules, according to another example embodiment of the present invention. The approach shown in FIG. 1B and discussed herein may be implemented using, for example, a tomography arrangement such as that shown in FIG. 1A and described above. At block 100, the tissue of a sample to be imaged is fixed. In some applications, the tissue is fixed via rapid freezing, chemical agents or a combination of the two fixation approaches. One approach to fixation is directed to high-pressure freezing. Another approach to fixation, useful in applications involving a biological specimen, involves paraformaldehyde fixation. Still other approaches involve one or more of chemical fixation and solvent replacement.

At block 110, the sample is embedded in a resin such as an acrylic resin, such as one of the commercially-available resins discussed above. In some applications, the sample is embedded with relatively low or minimal drying, extraction or permeabilization of the sample, and in other applications, fixation and/or embedding is carried out at relatively low temperatures (e.g., at about −40° C.) to retain lipids and other small molecules within the embedded specimen.

At block 120, the embedded sample is cut into very thin, or ultrathin, sections. In some applications, ribbons of thin (e.g, 50-200 nm) sections are cut from a resin block in which a sample is fixed. A variety of cutting approaches are used, and in some applications, an ultramicrotome such as the Reichert Ultracut E available from Leica, Deerfield, Ill., is used to cut the sections to form stable ribbons measuring up to centimeters in length on an air-water interface of a diamond-knife boat of the ultramicrotome. In some applications, a tacky adhesive such as Weldwood Contact Cement (available from DAP Inc., Dayton, Ohio) or Pliobond (available from Ashland, Inc., OH) is applied to the outer surface of the resin block prior to sectioning.

Figure 2:
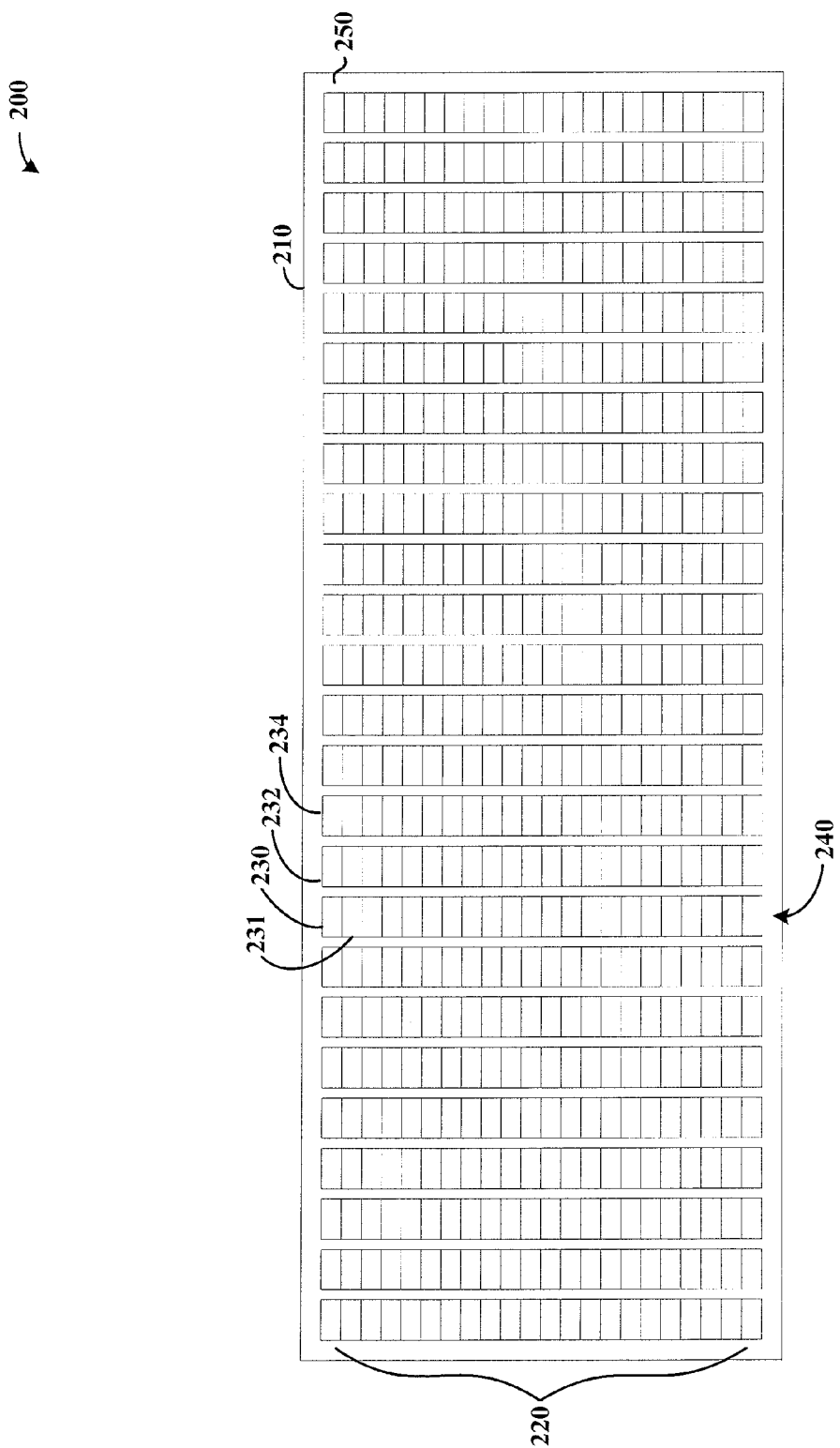
FIG. 2 shows an imaging arrangement for holding and arranging a sample, according to another example embodiment of the present invention.

At block 140, the sections are arranged in an ordered spatial array on a glass slide or, in some applications, on multiple glass slides. Where ribbons are cut, the ribbons are collected in a single layer (e.g., in closely spaced parallel rows) and bonded (e.g., coupled, fixed or otherwise attached by gentle heating) to a slice. In some applications, the water level in a diamond knife boat of an ultramicrotome is varied to facilitate the transfer of ribbons to the surface of a slide. One example approach for the ordering and spatial arraying of a sample on a slide is shown in FIG. 2, described below; one or more such slides may be used to fix and order slides from a particular sample.

In one particular embodiment where the specimen is to be imaged with scanning electron microscopy, the glass slide or coverslip is coated after applying the sample slices, to form an electrically conductive layer, for example, a carbon-coated layer.

In some embodiments, the glass slide is coated at block 130, prior to applying the sample slices (e.g., ribbons). In one implementation, the glass slide is coated to form a reflective surface to facilitate imaging. In another implementation, the glass slide is coated to form an electrically conductive layer to facilitate electron microscopic imaging. In still another implementation, the slide is coated with a substance to promote section adhesion or other desirable physical or chemical interaction with the sample section.

At block 150, the sample is stained using direct or indirect immunofluorescence, labeled cDNA probes, labeled toxins or lectins, or heavy metals. For instance, one or more of fluorescently-labeled antibodies, toxins, hybridization to fluorescently-labeled cDNA probes, RNA, or lipophilic membrane stains are used for different applications.

Once stained, some or all of the sample sections are imaged (and/or otherwise processed to collect data) at block 160 using one or more of optical, electron or probe microscopy, and mass spectrometry to obtain images or other sample data exhibiting relatively high resolution. In some applications, a combination of imaging approaches is used, such as a combination of optical and scanning electron microscopy, the latter implementing backscattered electrons, cathodoluminescence signals and/or scanning probe microscopy approaches. In this regard, an individual slide can be imaged via sequential application of multiple imaging modalities such as light, scanning electron and scanning probe microscopy approaches.

At block 170, the images are used to analyze the sample, such as by forming an image of the stained or otherwise labeled molecular arrangement of the sample, or involving an approach such as those implementing SEM, a polymerase chain reaction (PCR) amplification, or mass spectrometry. The analysis may involve the use of one or more imaging arrangements, with one or more processing and/or display arrangements to facilitate access to the images for human and/or machine interface. In some embodiments, individual slice images are aligned and/or de-warped to construct an accurate, high-resolution volumetric image stack representing the molecular structure of the sample and, in some implementations, multiple modalities of the sample.

In another example embodiment, after imaging at block 160 (and, in some applications, after analysis at block 170), the sample sections are washed or eluted at block 180, and the process continues again at block 150 with a re-staining approach, with subsequent imaging at block 160 and analysis at block 170. For various embodiments, this washing, re-staining and re-imaging cycle as indicated via blocks 180, 150 and 160 is repeated a multitude of times to analyze the sample under different staining and/or processing conditions.

In some embodiments, the images obtained at block 160 are used to facilitate molecular detection that is multiplexed across large numbers of antibodies and across multiple staining modalities (e.g., immunostaining, toxin and other stain chemistries, in situ hybridization and others) by staining alternate sections, rows or columns of sections with different agents, or by sequential stain-stripping or stain-bleaching and re-staining steps as indicated via blocks 180, 150 and 160.

In addition to the above approaches described in connection with FIG. 1B, the slides formed at block 140 are analyzed using one or more of a variety of other approaches, in connection with and/or as an alternative to the imaging approaches described above. For example, in some example embodiments, slides are analyzed using PCR reactions localized by microfluidics or gel layers. In other example embodiments, the slides are analyzed by laser, electron or ion ablation with mass spectrometry.

FIG. 2 shows an imaging arrangement 200 for holding and arranging a sample, according to another example embodiment of the present invention. The arrangement 200 includes a slide 210 made from glass or another appropriate material, and an array 220 of individual slices from a sample is bonded to the slide. By way of example, single slices 230, 231, 232 and 234 are labeled for reference, with the slices 230 and 231 being in column 240, and slices 230, 232 and 234 being in row 250 of the array 220. The slices are arranged in the array 220 and coupled to the slide 210 using one or more of a variety of approaches, such as those shown in and described in connection with FIG. 1B above.

In some applications, the sample slices in the array 220 are serially sliced to form ribbons that are arranged on the slide 210. For instance, each column (e.g., including column 240) is formed from a single ribbon in certain embodiments. In other embodiments, each row (e.g., including row 250) is formed from a single ribbon. In this regard, the spacing and placement of each individual specimen may vary in accordance with the implementation of a ribbon of slices of a particular sample.

Referring to both FIG. 1B and FIG. 2 and implementing both figures in connection with another example embodiment of the present invention, the staining approach at block 150 and subsequent imaging at block 160 are directed to the analysis of a specific portion of a sample sliced and arranged on the slide 210. A stain or other treatment is selectively applied to a portion of the slices in the array 220 to facilitate a particular type of analysis. In one application, for example, a wet chemical analysis approach involving PCR reactions is confined to a relatively small volume using one or more microfluidic chambers to selectively direct material to the slices in the array. The corresponding images obtained from the slices are used to characterize any response or labeling that relates to the microfluidic confinement.

Other aspects of the present invention involve immunofluorescence staining of ultrathin resin-treated sections. Such post-embedding immunofluorescence can be realized by labeling resin-treated sections of brain tissue. To illustrate the degree of this staining, in particular embodiments (e.g., for experimental purposes), sections are as thin as about 0.06 μm and not thicker than about 0.2 μm in some applications, and not thicker than about 1 μm in other applications; the effective lateral resolution can be illustrated using antigens known to have dense distribution in such tissues. With immunofluorescent detection of synapsin and α-tubulin in the adult mouse cerebral cortex, individual presynaptic boutons and microtubule bundles can be easily resolved. A number of other antigens can also be reliably recognized by antibodies in resin-treated sections. The improved lateral resolution of this immunostaining method facilitates determining the spatial relationship of different antigens. Double immunofluorescence labeling of synapsin and PSD-95 reveals the complementary distribution of these two proteins, which are known to be adjacent to each other with no overlap. The thinness of the sections ensures the improved image resolution, but the 3D distribution and relative localization of antigens are not readily determined from single sections. For example, orphan synapsin and PSD-95 puncta may be present, but because the sampled volume is thinner than the immunoreactive structures themselves, their partner (corresponding portion of the synapsin and/or PSD-95 puncta) could be located above or below the sampled tissue.

Figure 3:
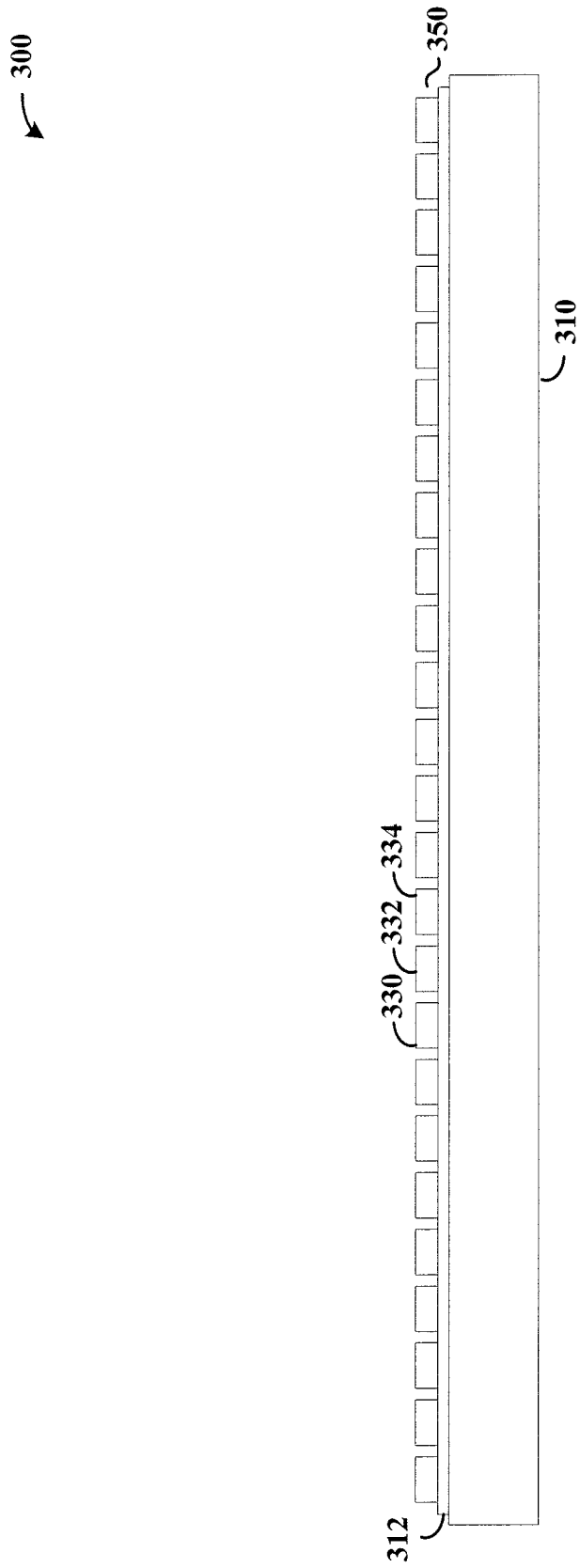
FIG. 3 shows a cross-sectional view of an imaging arrangement for holding and arranging a sample, according to another example embodiment of the present invention.

FIG. 3 shows a cross-sectional view of an imaging arrangement 300 for holding and arranging a sample, according to another example embodiment of the present invention. The arrangement 300 may, for example, represent an example cross-sectional view of row 250 in the arrangement 200 of FIG. 2; in this regard, various items in FIG. 3 are labeled similarly to those in FIG. 2 as may correspond for certain embodiments.

The arrangement 300 includes a microscope slide 310 for holding a multitude of sample slices in place for imaging. A layer 312 is optionally formed on the slide, prior to application of sample slices, and includes one or more of a variety of materials to facilitate various example embodiments. For instance, as discussed in connection with block 130 of FIG. 1B, the slide layer 312 may include one or more of a reflective material, an electrically conductive material, a substance to promote section adhesion, or a material that promotes other desirable physical or chemical interaction with the sample slices.

The slide 310 (and layer 312, when implemented) hold sample slices such as those shown in a row 350, with individual slices 330, 332 and 334 labeled by way of example. These slices are each in a column (i.e., perpendicular to the cross-sectional view in FIG. 3) of slices, which corresponds to a ribbon or other slice approach as implemented with a sample specimen.

Sections can be imaged on a Zeiss Axioplan fluorescence microscope using a Zeiss 100x/1.4 NA Plan ApoChromat objective or 100x/1.3 NA Plan NeoFluar objective and a Zeiss AxioCam MRm camera. Using commercially-available or open-source computer-software application for image processing/analysis, images from serial sections can be converted to stacks, aligned and used to reconstruct a three-dimensional view of the specimen. For example, using the open-source software "ImageJ", the Enhance Contrast and Subtract Background functions can be used for image processing, then the images from the serial sections can be converted to stacks and aligned with the StackReg plugin software in ImageJ. The aligned image stacks can then be characterized (e.g., volume rendered) with computer-based three-dimensional visualization and modeling technology, such as well-known volumetric rendering (e.g., Amira 4.0) graphics tools.

Figure 4:
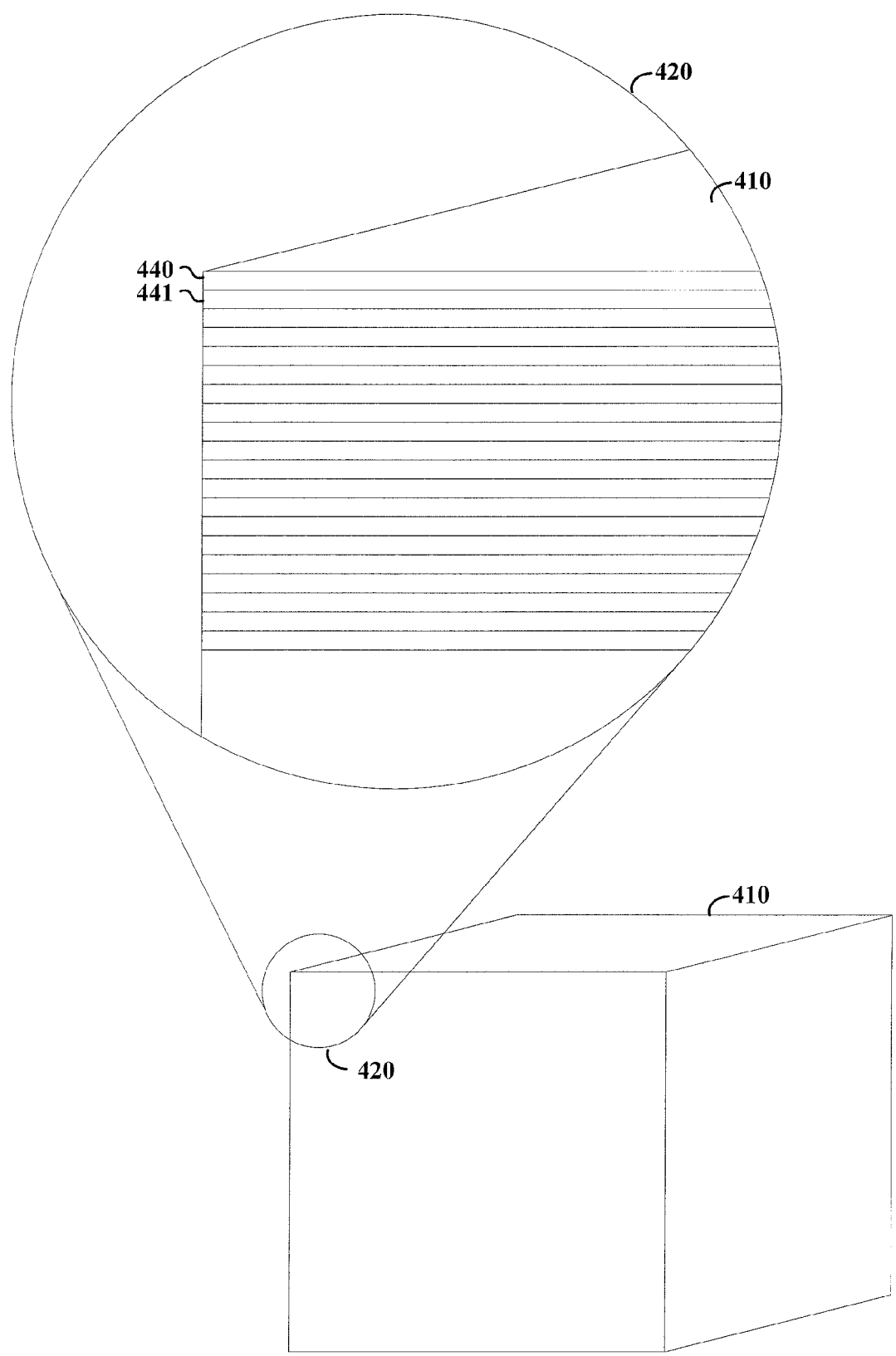
FIG. 4 shows a three-dimensional view of embedded tissue block of a biological specimen, according to another example embodiment of the present invention.

FIG. 4 shows a three-dimensional view of an embedded tissue block 410 of a biological specimen, according to another example embodiment of the present invention. An inset view 420 shows an upper corner of the tissue block 410 in greater detail. The tissue block 410 is a portion of a biological sample, such as brain tissue from a subject, that is removed from the subject, set using an approach such as those described above (e.g., using chemical and/or temperature approaches) and embedded in a resin.

Referring to the larger inset view 420, a multitude of slices are made from the block 410, with each slice shown as a lateral cut with individual slices including slices 440 and 441 labeled by way of example. Note that while all slices are shown for illustrative purposes, the slices are generally removed and placed on an imaging arrangement, such as a slide. For instance, in some embodiments, the slices from the block 410 are processed in a manner similar to that shown in and described in connection with FIG. 2 and FIG. 3 above. Slices 440 and 441 are labeled for illustration; relative to FIG. 2, slice 440 may correspond to slice 230, and slice 441 may correspond to slice 231, both arranged in column 240.

Figure 5:
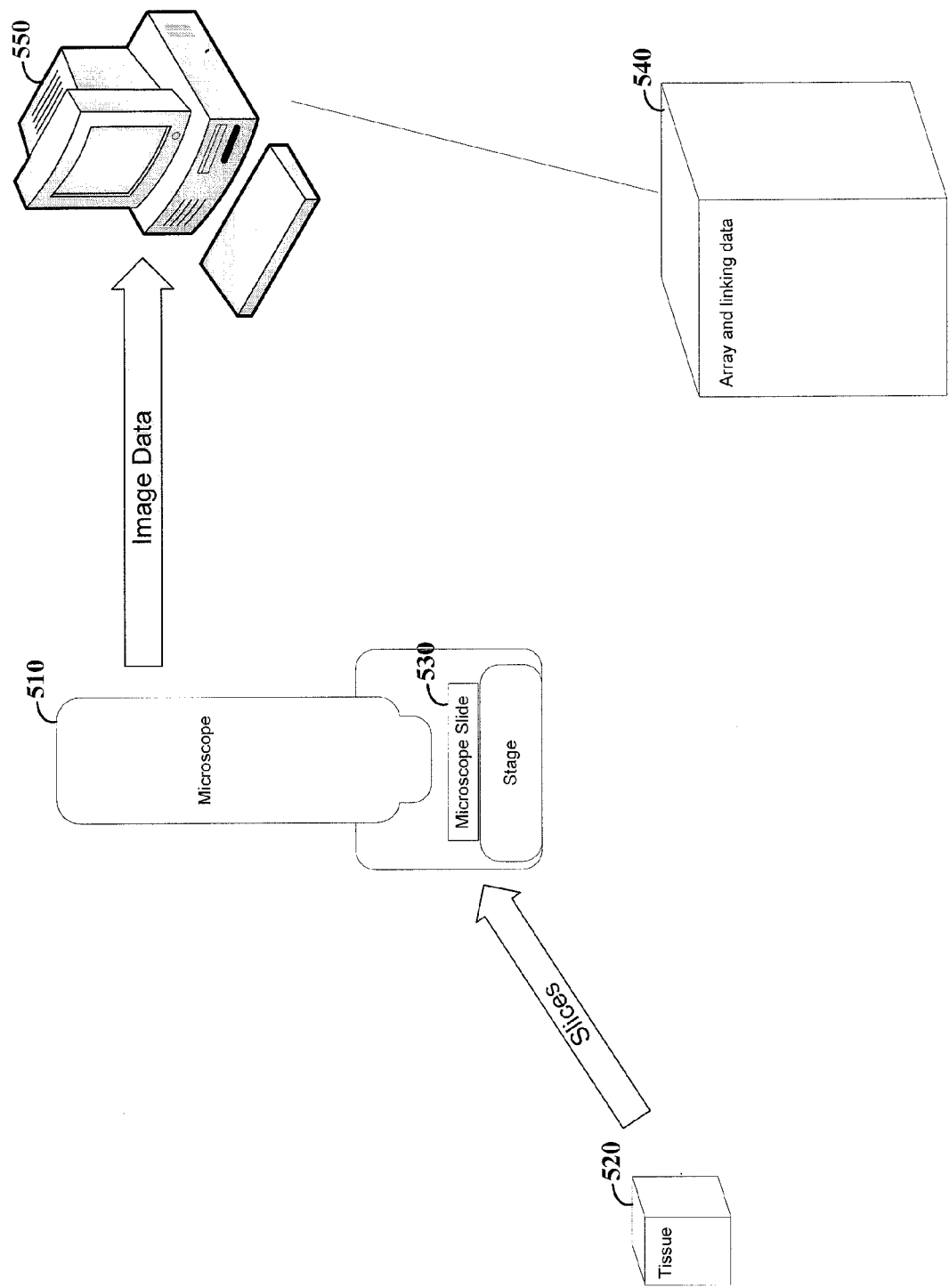
FIG. 5 shows a system for imaging a biological sample, according to another example embodiment of the present invention.

FIG. 5 shows a representation of systems for imaging a biological sample, according to other important aspects of the present invention. In one example embodiment, a system includes a fluorescence microscope arrangement 510 to image a tissue specimen 520 that is sliced and arranged in an array on a slide 530 (e.g., as may be similar to slide 210 in FIG. 2). Data corresponding to the ordering of the tissue slices on the slide 530 is stored in a three-dimensional database 540 that indicates (and correlates) data for individual slices in an array. This data includes, for example, data characterizing the tissue to which the slice applies, the arrangement of slices relative to each slice's location in the array, and any linking data relative to other slides (e.g., where slices of the tissue specimen 520 are arranged on two or more slides).

The fluorescence microscope arrangement 510 collects image data from the slide 530 and passes that image data to a computer arrangement 550 for processing. The computer arrangement 550 accesses the three-dimensional database 540 to retrieve array and linking information for the image data and uses the retrieved information to construct a three-dimensional image of the tissue specimen 520.

While shown implemented with a single microscope arrangement 510 and single processing arrangement 550, the approach shown in FIG. 5 is implemented with two or more such arrangements to facilitate, for example, processing and analysis of multiple slides for a common tissue specimen, or for obtaining different types of images from the slide 530. In this regard, the three-dimensional database 540 is accessible by different CPUs (or other processors) to create a three-dimensional image of the tissue specimen 520 using one or more microscope arrangements.

In connection with the arrangement and approach shown in FIG. 5, or as otherwise described herein, various example embodiments are directed to systems, arrangements, and computer-executable data for creating images. For example, one embodiment is directed to computer-executable data in a storage medium to link sample slices and facilitate the three-dimensional arrangement and reconstruction of an image corresponding to a sample from which the slices are obtained.

Figure 6:
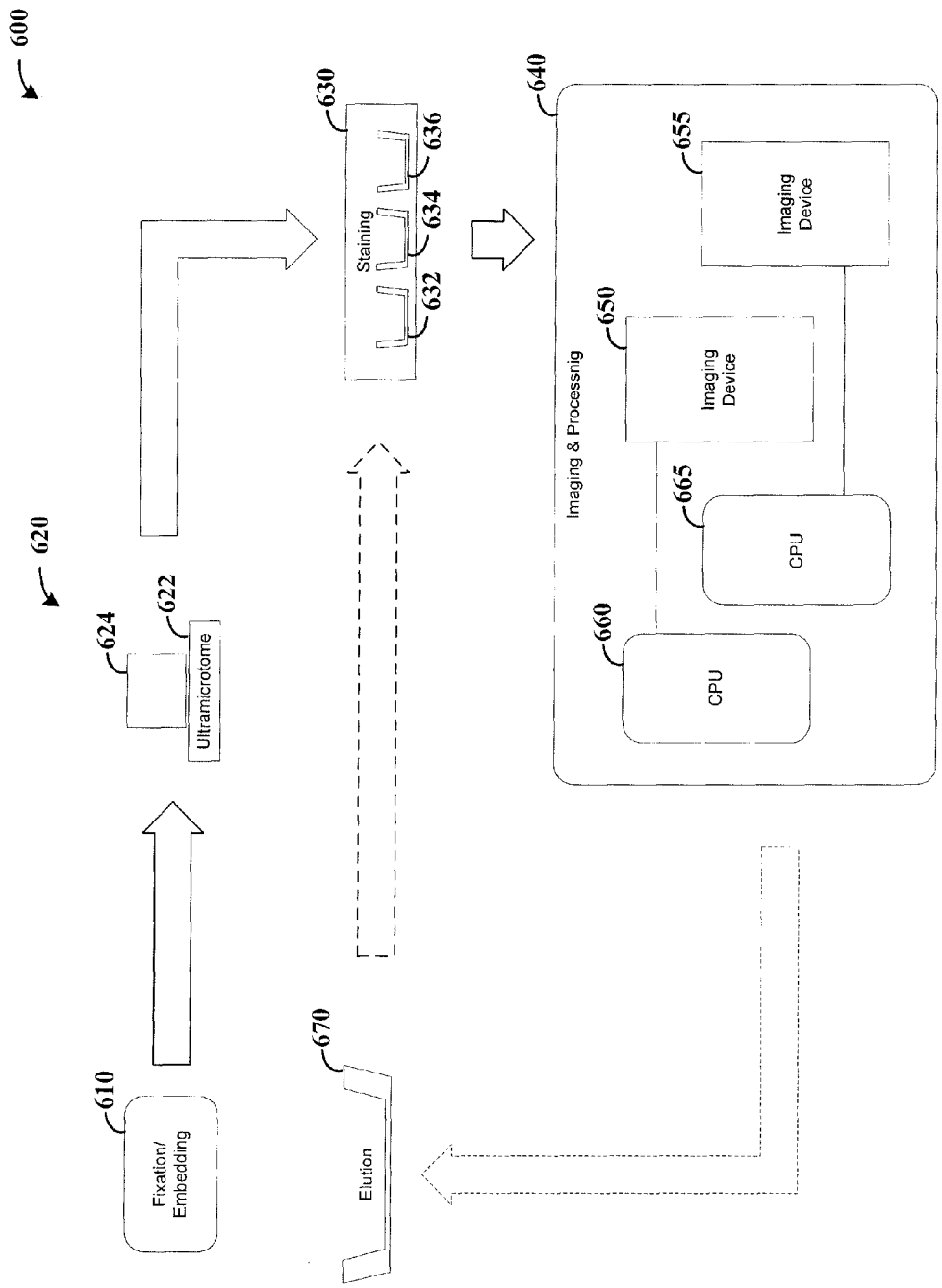
FIG. 6 shows a system for imaging a biological sample, according to another example embodiment of the present invention.

FIG. 6 shows a system 600 for imaging a biological sample, according to another example embodiment of the present invention. In various applications, aspects of the system 600 in FIG. 6 may be implemented using the devices and approaches shown in connection with system 500 in FIG. 5. The system 600 includes a fixation/embedding arrangement 610 for fixing (e.g., freezing and/or chemically treating) a sample and embedding the sample in a resin. The fixation arrangement 610 is shown generally in that a multitude of fixation approaches may be implemented in connection with FIG. 6. However, for various embodiments, the fixation arrangement 610 includes one or more of a sample holder, a resin supply, a solvent supply and a temperature controlling device. A slicing arrangement 620, such as an ultramicrotome with a sample holder 622 and knife arrangement 624 (as discussed above), is arranged to slice the fixed sample and, where appropriate, facilitate the arrangement of the sliced sample onto a slide or other medium upon which the sample can be located for analysis.

A staining arrangement 630 is adapted to stain sample slices as fixed to a slide or other arrangement. In some applications, the staining arrangement 630 is adapted to apply two or more different types of stain to a sample for a single imaging cycle or in subsequent staining cycles. To facilitate the application of different stains, stain material holders 632, 634 and 636, or other stain application devices, are implemented with the staining arrangement 630.

The system 600 further includes an imaging and processing arrangement 640, including with one or more imaging and processing devices, depending upon the application. Microscopy devices 650 and 655, and two image processing CPU's 660 and 665 are shown here by way of example. In some applications, each of the imaging devices 650 and 655 is similar and facilitate simultaneous imaging of different slices that may, for example, correspond to different slices from a single sample, to speed the imaging process. In other applications, the imaging arrangements 650 and 655 are adapted to facilitate different imaging approaches that may, for example, be used with a single sample (e.g., an optical fluorescence device and a scanning electron microscopy (SEM) device).

Image data obtained via the one or more imaging arrangements is provided to an analysis device 660 such as a computer. In some applications, a second analysis device 665 is also used and facilitates the separate processing of image data from different imaging arrangements. This approach is useful, for example, where a sample is sliced and placed onto two or more slides, with image data from the separate slides collected at different imaging arrangements 650 and 655, processed at analysis devices 660 and 665 and, where appropriate, combined via communications between the analysis devices to form a single three-dimensional image.

In some applications, the system 600 also includes a rinsing or eluting arrangement 670 that facilitates rinsing of the slides after imaging, and further for use in re-staining at the staining arrangement 630. The rinsing arrangement 670 may, for example, hold or otherwise apply a rinse agent to a sample; in this regard, the shown arrangement 670 is implemented in different forms for various example embodiments.

In connection with neurological applications, array tomography imaging is automated with puncta quantification as follows. Serial section arrays are imaged using commercially available software such as AxioVision 4.6 from Carl Zeiss Microimaging. A multichannel volume image is collected by imaging an array of a multitude of sections from a layer of a cerebral cortex of a subject, immunostained with one or more antibodies (e.g., to synapsin I and to GFP). Multiple separate fluorescence images (e.g., three color channels) are acquired under full, unattended automation using an image-based automatic focus algorithm. These renderings exhibit high axial resolution and depth-independence of array tomography over large volumetric fields of view, such as those up to and exceeding 120 μm×110 μm×27 μm. Monochrome rendering of fluorescence (e.g., anti-GFP fluorescence) reveals intricate detail of the specimen. For example, the dendritic spines lining the dendrites, as well as the thin axons crossing the tissue are clearly visible using this approach. Also, individual synapsin puncta can be clearly resolved and counted using a software-based or other approach as facilitated by the high detail imaging made possible in connection with these approaches. Similarly, synapsin puncta can be counted in layers of the somatosensory cortex of a subject such as a control mouse. Thus, these approaches to the automation of array tomography allow for fast and precise imaging as well as quantification of arrays, and are applicable to relatively large tissue volumes.

In connection with other example embodiments, various discoveries relating to array tomography have been made and, in some embodiments, unexpected results have been obtained. For example, conventional fluorescent dyes show remarkable photostability under the conditions of array tomography as described herein. In one application, after 6 minutes of constant illumination with a 100 W mercury lamp, 85% of the initial fluorescence intensity remained for certain samples, which may involve mitigation of undesirable photobleaching mechanisms. Where resin is used to fix or set the sample being analyzed, the relative rigidity of the resin can be used to restrict the mobility of molecules and contribute to photostability, which promotes the collection of high-quality images using long exposure times.

In connection with another embodiment, antibodies are used to penetrate to a depth of about 200 nm in LRWhite-embedded material, thus increasing the amount of accessible antigens and allowing for an uninterrupted 3D reconstruction from serial sections as thick as 200 nm. Conditions such as resin polymerization (e.g., relatively slow thermal polymerization) can be employed to limit crosslinking and lead to linear molecular arrangement, thus facilitating antibody penetration.

Other aspects of the invention facilitate immunoimaging by way of elution approaches that can be carried out while maintaining the tissue undergoing analysis in condition for analysis. LRWhite ultrathin sections on glass slides are a favorable substrate for antibody elution and can undergo a large number of sequential cycles of staining, imaging, stripping, and re-staining. In this context and in connection with various embodiments, quantitative staining is carried out for multiple cycles (e.g., at least nine cycles), and in other embodiments, much more than 9 cycles.

The array tomography approaches described herein offer access to important aspects of neural circuit molecular architecture that were formerly difficult to visualize and measure within tissue specimens. In some embodiments, array tomography is used to achieve easy and efficient resolution and quantification of individual synapsin immunolabeled puncta throughout large volumes of mature central nervous system neuropil. Synapsin is used as a reliable marker for synapse characterization and as a marker in array tomography for synapse quantification. With these approaches, changes in the numbers and volume densities of synapses can be detected and used to understand human neurological and cognitive disorders. Furthermore, since immunofluorescence and SEM array tomography lend themselves well to imaging human tissues, array tomography is used both for the direct study of human clinical specimens and for critical comparisons of human and animal disease-model tissues, in connection with various example embodiments. Other applications use the compatibility of GFP-based imaging approaches with array tomography to study transgenic animals and to complement and extend in vivo imaging techniques with retrospective high-resolution analysis by array tomography. Relative to brain tissue molecular architecture and ultrastructure, certain array tomography embodiments involve the molecular classification of neural cell types, the determination of ion channel and receptor distributions within the tissue context, and circuit connectivity.

According to another example embodiment, an automated electron microscopy approach involves segmentation and machine learning algorithms with an array tomography approach as described herein, with applications to the characterization and, in some embodiments, reconstruction of neurological circuits. A specimen is sliced and arranged, for example, as described with and shown in FIGS. 1-5. An image processing program automatically tunes its operation based on training sets of data by pairing raw electron microscopy images and corresponding manual segmentation results. After the assimilation of a sufficient quantity of sufficiently accurate training data (e.g., depending upon the application and available tools), the learning algorithm automatically and reliably segments new image data that is generally similar to that presented by the training sets. Array tomography is used to produce training sets of sufficient size and accuracy to train a robust and reliable learning algorithm.

In some applications, conjugate, voxel-registered immunofluorescence (IF) and electron microscopic (EM) volume images are obtained (e.g., by array tomography) and used to help to solve EM segmentation problems that can be present with tissue analysis, merging the molecular discrimination strengths of IF imaging with the high resolution strengths of EM. For instance, array tomographic IF image data can be used to pinpoint synapses and to discriminate cell-specific axonal and dendritic tags in a specimen and thus pass helpful prior information to an EM segmentation algorithm. Low-resolution but cell-specific optical information (e.g., from a brainbow mouse) can be very useful to the successful detection and avoidance of skipping errors related to skips from one fine axon to the next when attempting to track densely packed axons over distance in EM segmentation. Large and accurate EM segmentations training sets derived from conjugate IF/EM tool data sets can be used as large and highly accurate training sets to refine segmentation algorithms that might learn eventually to segment and interpret data sets comprising EM data alone. That is, such algorithms are used to reconstruct a circuit using a fully automated EM technique, such as SBFSEM, and to reconstruct human cortical circuits.

With these approaches, mammalian cortical circuit structure can be reconstructed for analysis or other purposes. In some embodiments, a rodent "whisker barrel" is reconstructed, defining the morphologies of all neural arbors, all the sites of potential synaptic contact, and as many details of circuit molecular architecture as possible. The whisker barrel is a patch of rodent sensory-motor cortex that processes information associated with one contralateral whisker (vibrissa), and is one component of a closely-packed somatotopic array of barrels, with one barrel per whisker. Each barrel occupies a columnar volume (e.g., just under about 0.5 mm in diameter and about 1.2 mm in height, and includes approximately 15,000 neurons and 100 million synapses). The barrel circumscribes a volume within which nearly all dendritic arbors are complete and where lateral connectivity within barrels is far denser than that between barrels. The associated peripheral sensory-motor structure, a single vibrissa, is also imaged and as such is tractable to functional study. Certain applications are directed to the reconstruction of two or more whisker barrels for various analysis approaches, such as to analyze the degree of structural stereotypy between functionally homologous cortical circuit components.

In some embodiments, transgenes are used to encode eight cell-marking epitope tags that allow most or all nearby cells to be distinguished by brainbow-style immunofluorescence as discussed, for example, in Livet, J, Weissman, T. A. Kang, H., Draft, R. W., Lu, J, Bennis, R., Sanes, J. R. and Lichtman, J. W., "Transgenic strategies for combinatorial expression of fluorescent proteins in the nervous system" in Nature 450, 56-62 (Nov. 1, 2007), which is fully incorporated herein by reference. An array comprising an entire whisker barrel cut into 50 nm sections is fabricated on standard microscope slides, and array tomographic immunofluorescence is used to discriminate antibody channels (e.g., 36 channels, of which eight are used to read the transgenic epitope tags and the remaining 28 are used to read endogenous molecules useful for classifying and modeling neurons and synapses). An imaging approach such as BsSEM imaging (backscattered electron scanning-electron microscopy) is used to read the ultrastructure of tissue sections in enough detail to meaningfully measure spine necks and to generate useful learning algorithm training sets.

The approaches described herein may be implemented in connection with and/or use a variety of analysis approaches and systems. In this context, for general information regarding sample analysis, and for specific information regarding analysis, staining and imaging approaches and devices that may be implemented in connection with one or more example embodiments herein, reference may be made to U.S. patent application Ser. No. 11/408,139, entitled "Optical Imaging of Molecular Characteristics of Biological Specimen" and filed on Apr. 20, 2006, which is fully incorporated herein by reference. In addition, for general information regarding applications in tissue analysis, and for specific information regarding neurological applications to which various example embodiments of the present invention may be directed, reference may be made to Kristina D. Micheva and Stephen J Smith, "Array Tomography: A New Tool for Imaging the Molecular Architecture and Ultrastructure of Neural Circuits" in Neuron 55, 25-36, Jul. 5, 2007, upon which aspects of the present invention are based and which is also fully incorporated herein by reference.

In connection with another example embodiment, tissue is imaged via three-dimensional volume imaging using serial sections formed into relatively long series of ribbons. The tissue is embedded in a resin, such as the commercially-available resins described above, and sectioned thinly into a long series of sections to form ribbons. The thin sections are immunostained, the stained sections are imaged and the images from the same region of each section are collected and aligned for 3D (three-dimensional) reconstructions with both a lateral field of view and a view of a serially-arranged slice. In some applications, this approach is used to image the relative distribution of different antigens via high 3D resolution. For example, one implementation is directed to the labeling of presynaptic boutons with synapsin, and their respective postsynaptic densities are labeled with PSD-95; the labeled sample is tracked through several ultrathin sections and the data is used to obtain a 3D image of their spatial relationship.

In another example embodiment, small and densely distributed objects within a tissue volume are quantified. In one implementation, individual synaptic boutons in an adult brain are resolved using 3D reconstructions from immunolabeled thin LR White sections (e.g., 60-200 nm), via resolution of individual synapsin labeled structures and the resolved structures are reliably quantified. Using planar immunofluorescence on serial sections of the adult brain, microtubule bundles are tracked and used to reconstruct the microtubule cytoskeleton of cells within tissue.

In another example embodiment of the present invention, immunofluorescence can be used to enhance the imaging of samples exhibiting relatively few antigens. This approach is useful, for example, with sample generally exhibiting a weak response due to the relatively thin nature of slices of the sample being imaged. The signal obtained via imaging is enhanced using a tertiary antibody with the same excitation/emission spectrum as the secondary antibody and directed towards the host species of the secondary antibody. Using immunofluorescence enhancement and 3D reconstruction, high resolution details are obtained for the relative distribution of samples such as the Kv2.1 channel and synapsin in a rodent cortex.

In connection with another example embodiment of the present invention, a consecutive staining approach is implemented with antibody elution. LR White sections of a sample are stained with an immunofluorescence stain, imaged and then applied and imaged antibodies are eluted. The sample is then stained with a different combination of antibodies. Using this approach, the majority of examined antigens survive the elution procedure and are detected again with almost identical distribution and very similar intensity of the signal. In some application, multiple consecutive rounds of staining, imaging and elution are performed to obtain information about the relative distribution of a significant number of antigens (e.g., 10 or more).

Alignment of slices, such as different slices on a common slide or a common slice imaged via subsequent staining, is carried out in one or more of a variety or manners. In one implementation, one of the antibodies from a first staining round (e.g., synapsin or tubulin) is included in each subsequent staining round. Images obtained for each immunostaining round are aligned using the included (repeated) antibodies, which are imaged for each round. Using the repeated antibodies, the spatial distribution of all antigens probed are mapped.

In another example embodiment, an approach to imaging a sample involves the preservation of the fluorescence of green fluorescent protein (GFP) and its variants (such as YFP) from staining round to staining round. The sample tissue is partially dehydrated (e.g., up to 95% ethanol) before embedding in a resin to preserve retention of bright GFP fluorescence.

In some implementations, LR White sections (e.g., 60 nm-200 nm in thickness) are treated with GFP before fixation and embedding, dehydrated and used in combination with immunostaining to image the distribution of antigens within identified cells. Also, for certain implementations, the relatively bright GFP signal is used for alignment between sections. A GFP antibody can be used on the thin sections to localize the GFP if its fluorescence is not sufficiently bright.

In another example embodiment, a correlative scanning electron microscopy (SEM) approach is implemented for imaging sections of a sample in connection with an imaging approach as described herein. In one instance, arrays of resin-treated sections mounted on glass slides are imaged via immunofluorescence and further imaged with a scanning electron microscope. Where appropriate, a stain or other labeling approach that facilitates SEM is implemented. For instance, heavy-element ultrastructural stains, antibody tagging particles such as colloidal gold or cathodoluminescence markers such as phosphor particles or quantum dots are used with various applications involving SEM combined with another imaging approach such as an optical fluorescence imaging approach. Information about the spatial distribution of different antigens obtained via fluorescent microscopy is combined with information about the structural details of the tissue obtained via the SEM.

In one implementation, a combined immunofluorescent-SEM approach involves the preservation of relatively fine structural details of the sample undergoing analysis. The tissue is processed in a way that is similar to processing for conventional electron microscopy, using both paraformaldehyde and glutaraldehyde for fixation and adding postfixation in osmium tetroxide before dehydrating the sample.

As an experimental embodiment, three adult mice (C57BL/6J), one YFP-H adult mouse (Feng, Mellor et al. 2000) and one adult Sprague Dawley rat are used. The animals are anesthetized by halothane inhalation and their brains quickly removed and placed in HBSS (4° C.). The cerebral cortex is dissected out and fixed by immersion in 4% paraformaldehyde and 2.5% sucrose in phosphate-buffered saline (PBS) using rapid microwave irradiation (e.g, using PELCO 3451 laboratory microwave system available from Ted Pella of Redding, Calif.; one cycle of 1 min on—1 min off—1 min on at 100 W, and two cycles of 20 s on—20 s off—20 s on at 350 W) and ColdSpot (e.g., Ted Pella) set at 15° C. The tissue is then left in the fixative for 30 minutes at room temperature or overnight at 4° C. After rinsing in PBS containing 3.5% sucrose, the tissue is quenched in 50 mM glycine in PBS and then dehydrated in a graded series of ethanol (45 seconds each at 350 W in microwave). For the YFP—H mouse, to preserve YFP fluorescence, the tissue can be dehydrated up to about 95% ethanol. The tissue is then infiltrated in (e.g., LR White) resin (3 times 45 seconds each at 350 W, and overnight at 4° C.), embedded in gelatin capsules and polymerized at about 50° C. For scanning electron microscopy (SEM), the tissue is processed as described above except that the fixative contained 0.1% glutaraldehyde and, before dehydration, a post-staining step with osmium tetroxide (1%) and potassium ferricyanide (1.5%) is added (3 cycles of 1 minute on—1 minute off—1 minute on at 100 W, followed by 30 minutes at room temperature).

Thin sections (60 nm or 200 nm) of resin-treated sections can be cut with an ultramicrotome (e.g., Ultracut E, Reichert Jung). For cutting ribbons of serial sections, after trimming of the biological "block" into a pyramid shape, glue (e.g., Weldwood Contact Cement diluted in xylene) can be applied with a paint brush to the top and bottom sides of the block. After the glue has dried (e.g., for about 2 minutes), a series of 30 or more sections are cut in ribbons using a Jumbo Histo Diamond Knife (Diatome). The ribbons can be mounted on subbed glass slides (coated with 0.1% gelatin and 0.01% chromium potassium sulphate) and placed on a hot plate (for about 60° C.) for 30 minutes. While dependent on environmental factors, the slides can typically be stored at room temperature for at least 3 months.

For immunofluorescence staining, the sections can be encircled with a PAP pen (ImmmEdge Pen, Vector Laboratories, Burlingame, Calif.) and their position are marked with a diamond knife on the opposite side of the slide. Unless stated otherwise, the sections can be pretreated with 50 mM glycine in Tris buffer (pH 7.6) for 5 minutes and the primary antibodies are applied diluted in Tris buffer containing 1% BSA (in some cases 1% donkey serum) for 2 hours. Secondary antibodies in Tris buffer with 1% BSA or 1% donkey serum are applied for 30 minutes. Between steps, the sections are extensively washed with Tris buffer. The sections are mounted using Vectashield (with or without DAPI, Vector Laboratories). To elute the applied antibodies, the mounting medium is washed away with $dH_2O$ and a solution of 0.15M $KMNO_4$ and 0.01 N $H_2SO_4$ is applied for 1:30 minutes (Tramu, Pillez et al. 1978). After an extensive wash with $dH_2O$, the slides are placed on a hot plate (60° C.) for 30 minutes. For subsequent viewing in SEM, the mounting medium is washed with distilled $H_2O$, the sections are placed on a hot plate (60° C.) for 30 minutes and then poststained with 5% uranyl acetate in $H_2O$ for 5 minutes and lead citrate for 90 seconds.

Microscopy and image processing steps follow as described above.

The various embodiments described above and shown in the figures are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For example, variation in thickness of slices, platforms (or slides) upon which slices are arranged, analysis/imaging tools and/or treatment approaches, characterize various other example embodiments. In the context of the approaches describing and implementing staining, the term stain is implemented to include a treatment used to mark or identify tissue; such treatment may or may not necessarily stain a specimen relative to conventional (e.g., coloring) or other characteristics often associated with a stain. Such modifications and changes do not depart from the true spirit and scope of the present invention, including that set forth in the following claims.

What is claimed is:

1. A method for imaging a biological specimen, the method comprising:
    embedding the specimen to set a molecular arrangement therein;
    thinly slicing the embedded specimen to provide a multitude of thin physical slices, having respective slice thicknesses defined between upper and lower surfaces of the respective slices of the specimen;
    serially arranging and fixing the physical slices in an array on a microscopy slide, therein forming an array of a multitude of slices;
    applying a stain to the physical slices;
    collecting image data from the slices on the slide, the image data including imaged portions of the specimen extending from the upper surface to the lower surface of each slice;
    using the image data and a known serial arrangement of the physical slices to combine image data from different slices to construct a three-dimensional image of the specimen; and
    after collecting image data, eluting the slices on the slide and repeating the steps of applying a stain and collecting image data with the eluted slices, wherein using the image data and a known serial arrangement of the slices to combine image data from different slices to construct a three-dimensional image of the specimen includes using image data from the slices before and after elution.

2. The method of claim 1, wherein repeating the step of applying a stain includes applying at least one different stain, relative to staining prior to elution, to facilitate imaging of a characteristic of the specimen that is different than characteristics imaged from the specimen prior to elution.

3. The method of claim 1, wherein repeating the step of applying a stain includes applying a stain that is common to the stain applied, prior to elution, further including using image data corresponding to the common stain to align images of the slices obtained, prior to elution, with images of the slices obtained after elution and re-application of stain to the slices.

* * * * *